United States Patent [19]

Walinsky et al.

[11] Patent Number: 5,109,861
[45] Date of Patent: May 5, 1992

[54] INTRAVASCULAR, ULTRASONIC IMAGING CATHETERS AND METHODS FOR MAKING SAME

[75] Inventors: Paul Walinsky, Philadelphia; Peter A. Lewin, Wyndmoor; John M. Reid, Strafford, all of Pa.

[73] Assignees: Thomas Jefferson University; Drexel University, both of Philadelphia, Pa.

[21] Appl. No.: 344,919

[22] Filed: Apr. 28, 1989

[51] Int. Cl.$^5$ ............................................. A61B 8/12
[52] U.S. Cl. ............................................. 128/662.06
[58] Field of Search ................. 128/662.06, 660.03, 128/662.05, 662.03

[56] References Cited

U.S. PATENT DOCUMENTS

| | | | |
|---|---|---|---|
| 3,542,014 | 11/1970 | Peonneau | 128/2 |
| 3,779,234 | 12/1973 | Eggleton et al. | 128/2 |
| 3,827,115 | 8/1974 | Bom | 29/25.35 |
| 3,938,502 | 2/1976 | Bom | 128/2 |
| 4,142,412 | 3/1979 | McLeod et al. | 73/194 |
| 4,232,373 | 11/1980 | Jackson et al. | 364/572 |
| 4,237,729 | 12/1980 | McLeod et al. | 73/861.25 |
| 4,259,870 | 5/1981 | McLeod et al. | 73/861.25 |
| 4,587,972 | 5/1986 | Morantte, Jr. | 128/660 |
| 4,589,419 | 5/1986 | Laughlin et al. | 128/663 |
| 4,637,401 | 1/1987 | Johnston | 128/663 |
| 4,665,925 | 5/1987 | Millar | 128/663 |
| 4,911,170 | 3/1990 | Thomas, III et al. | 128/662.06 |
| 4,911,172 | 3/1990 | Bui et al. | 128/662.06 |
| 4,917,097 | 4/1990 | Proudion et al. | 128/662.06 |
| 5,002,058 | 3/1991 | Martinelli | 128/662.06 |

OTHER PUBLICATIONS

American Heart Journal, pp. 332-341 (Feb. 1989).
Cole, J. S., "The Pulsed Doppler Coronary Artery Catheter", 56 Circulation, pp. 18-25 (Jul. 1977).
Martin et al., "An Ultrasonic Catheter Tip Instrument for Measuring Volume Blood Flow", IEEE Ultrasonics Conf. Proc., pp. 23-17 (1975).
B. Baizilai et al., "Quantitative Ultrasonic Characterization of Nature of Atherosclerotic Placques in Human Aorta", Circulation Research 60:459 (1987).
McPherson et al., "Delineation of the Extend of Coronary Atherosclerosis by High Frequency Epicardial Echocardiography", New E.J. of Med. 316, p. 304 (1987).
Meyer et al., "Feasibility of High-Resolution, Intravascular Ultrasonic Imaging Catheters", Radiology 168:113-166 (1988).
Hodgson et al., "Validation of a New REal Time Percutaneous Intravascular Ultrasound Imaging Catheter", American Heart Association Abstract, (Nov. 14-17, 1988).
Graham, "Utility of an Intravascular Ultrasound Imaging Device for Arterial Wall Definition and Atherectomy Guidance", American College of Cardiology Abstract (Mar. 19-23, 1989).
Kophock et al., "Intraluminal Vascular Ultrasound: Dimensional and Morphologic Accuracy Laser and Stent Therapy in Vascular Surgery", Int'l Congress II (Feb. 10-15, 1989).
Schwarten, et al., "Endovascular US: Adjunct to Percutaneous Atherectomy", Radiology Abstract 331.
"Ultrasound Imaging Catheter Hailed for Diagnostic Accuracy", Cardiology World News, p. 25 (Jul./Aug. 1988).

(List continued on next page.)

Primary Examiner—Francis Jaworski
Attorney, Agent, or Firm—Woodcock Washburn Kurtz Mackiewicz & Norris

[57] ABSTRACT

Novel intravascular, ultrasonic imaging catheters are provided which utilize thin layers of a flexible plastic material, such as PVDF, which can be spot polarized in active regions which are to serve as piezoelectric transducers. Thin layer metallic electrodes are deposited on opposing surfaces of these active regions. Strips of the appropriately configured material also having shielding and backing and/or core forming portions are spiral wound into a completed catheter. Alternatively, the catheters are fabricated from extruded PVDF tubing which may be formed around a central core which carries those electrodes which are to contact the inner surface of the extruded tube.

15 Claims, 3 Drawing Sheets

OTHER PUBLICATIONS

EndoSonics Cathscanner I System Trade Literature, EndoSonics Corp., Rancho Cordova, Ca.
Medical World News, Jan. 9, 1989, p. 33.
Moretti, M., "New Diagnostic Techniques Rely on Image Processing", Laser Focus/Electrooptics, pp. 198-203 (Apr. 1988).
CVR & R 20-21 (Jun. 1988).
Mallery et al., "Intravascular Ultrasound Imaging Catheter Assement of Normal and Atherosclerotic Arterial Wall Thickness", JACC vol. 11, No. 2 Abstract 22A (Feb. 1988).
Bom et al., "Intra-Arterial Ultrasonic Imaging for REcanalization by Spark Erosion", Ultrasound in Med. & Biol. vol. 14, No. 4, pp. 257-61 (1988).
A. S. DeReggi et al., JASA 69:853-859, 1981.

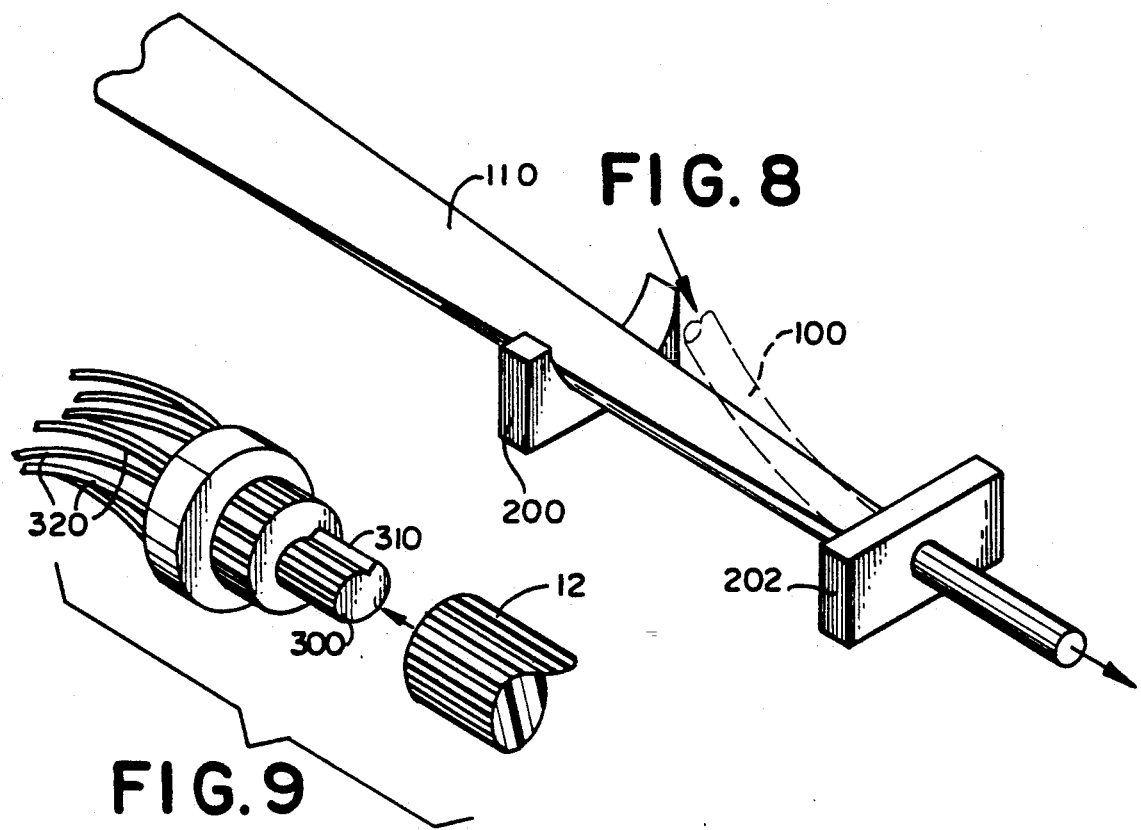
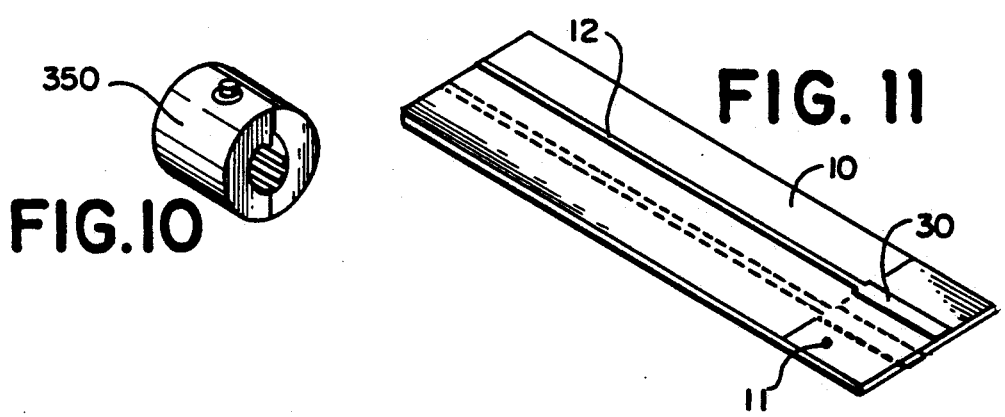

INTRAVASCULAR, ULTRASONIC IMAGING CATHETERS AND METHODS FOR MAKING SAME

FIELD OF THE INVENTION

The present invention relates to the field of devices which are used to diagnose the condition of the human vasculature, and more particularly to catheters which are designed to image arteries, veins, and other such structures.

BACKGROUND OF THE INVENTION

Angioplasty is a popular method of treating coronary artery disease without the dangers of surgery and anesthesia. However, the results range from excellent to disappointing. Therefore, there is a need to develop a new method of obtaining data on the lesion being treated which will aid in correlating the disease to the outcome of the treatment. Eventually this could provide guidance in patient selection, and in follow-on therapy that would make angioplasty more successful.

Vascular disease is the largest cause of death in this country. Vascular disease, which has as its end stage complete occlusion of the affected vessels, can cause stroke, heart attack, kidney failure or loss of limb in affected patients. New techniques are required to evaluate vascular disease and enhance our ability to study this problem, thereby allowing more effective diagnosis and permitting therapies to be administered safely Specifically, new methodologies are required to analyze the thickness of the vessel wall, the nature of the vessel wall, the integrity of the lining of the vessel, and to evaluate the presence of intraluminal thrombosis or atherosclerotic debris. Vascular disease is primarily caused by the development of a atherosclerotic plaque. As the plaque increases in size, there is either an eccentric or concentric disposition of atheromatoses in the vessel. With an encroachment of plaque on the vascular lumen, there is a restriction of blood flow through the vessel. At first this flow restriction occurs only during periods when increased flow is required. For example, even when there is a blockage in the arteries leading to the legs there is normal blood flow at rest, however, when walking, an increased blood flow is required. Pain will thus occur only during walking when the blockage in the vessel prevents the needed increase in flow through the narrowed blood vessel. As plaque development progresses, there may be further encroachment into the lumen of the vessel and a decrease in flow at rest may occur. Pathologic changes in the plaque such as splitting or lifting up of the plaque may initiate the formation of a thrombus which may then cause complete occlusion of the vessel. Such complete occlusion will then cause death in the tissue normally supplied by that vessel. For example, if the vessel is one of the heart's vessels, a heart attack will occur, or if the vessel is one leading to the brain, a stroke will occur. Although in the past little could be done to treat these problems, in recent years new therapeutic interventions have evolved. These include surgical removal of the plaque, bypass of the plaque, and balloon angioplasty in which a small balloon catheter is positioned across the stenosis and then inflated to crush the blockage. In addition, newer technologies are being developed including ablation of the plaque by a laser beam or removal of the plaque by miniaturized mechanical devices. Recently, Barry et al have suggested that radiofrequency generated thermal energy can have a substantial effect on the mechanical and histologic characteristics of the arterial wall, and may have implications for radiofrequency angioplasty. *American Heart Journal*, pages 332-341 (February 1989).

Most current vascular angiography techniques permit visualization only of the diameter of the vessel. Visualization of the entire vascular wall is not possible. Many devices and approaches have been suggested for such imaging of the human vasculature. Perhaps the most common approach relies upon intravenous injection of contrast media in combination with imaging from an external source. More recently, attention has been directed to imaging the walls of vessels to determine their thicknesses, particularly in relation to whether plaque growth has narrowed the lumen of a coronary artery such that treatment by angioplasty and/or by-pass is recommended.

There is, of course, a great need to accurately diagnose the condition of arteries such as the coronary arteries, and to do so in real time. Imaging of plaques is somewhat complicated in that not all plaques are calcified, and may not be imaged by certain imaging techniques. Such deficiencies in diagnostic visualization limit the knowledge of vascular pathology and hence, the understanding of the development and course of the disease process. In addition, selection of therapeutic interventions may be hindered because of these limitations. Currently, there is a 30% incidence of recurrence of stenosis following coronary balloon angioplasty. The process of restenosis is poorly understood. Investigation in the vascular wall may shed light on the mechanisms and course of such recurrence of such stenosis.

Full visualization of the vessel wall would also assist in understanding the base line anatomy and physiology of the vessel. Visualization is also needed to plan proposed therapeutic interventions and to determine the results of such interventions. Such visualization of the vessel should provide as close an approximation to the histologic cross section of the vessel as possible. Such a cross section should include delineation of the lumen of the vessel, any intraluminal masses or thrombosis, any tear in the wall in the vessel and delineation of the thickness of the vessel wall and the presence of calcium in the vessel wall.

An advantage of ultrasonic imaging is that relatively soft tissues can be imaged effectively, although the depth of imaging is somewhat limited. It has not proven to be possible, for example, to use external transducers to image coronary arteries of closed chest patients. On the other hand, were ultrasonic imaging possible in closed chest patients, it might be possible to locate soft tissue lesions and areas of uncalcified plaque which presently escape other diagnostic techniques.

Accordingly, it has been suggested to provide an ultrasonic probe or transducer to image the walls of vessels such as the coronary artery to determine whether undesirable thickening is present. In order to be effective, however, such probes must be miniaturized to diameters which will permit transcutaneous insertions into the vessel lumen. Additionally, such probes must exhibit sufficient flexibility to allow the required intravascular maneuvering to the target site.

Various investigators have suggested designs for ultrasonic imaging catheters. Some of these are intended merely to determine the volume or rate of flow of blood through the vessel lumen. U.S. Pat. No. 4,589,419

(Laughlin et al), U.S. Pat. No. 4,637,401 (Johnston), and U.S. Pat. No. 4,665,925 (Millar) disclose catheters using ultrasonic transducers to determine blood flow. In this regard, see also Cole, J. S., "The Pulse Endopoler Coronary Artery Catheter", 56 Circulation, pp. 18–25 (July 1977). See also Martin et al, "An Ultrasonic Catheter Tip Instrument for Measuring Volume Blood Flow", IEEE Ultrasonics Conf. Proc. pp. 23–17 (1975);

Other investigators have suggested designs which are intended to image an obstruction within the lumen itself, i.e. an obstruction "in front" of an advancing catheter. U.S. Pat. No. 4,587,972 (Morantte, Jr.) discloses one such design. These approaches, however, fail to image a section of the vessel, and therefore do not provide critical information about the thickness of the vessel wall at a given location.

Ultrasound has also been used in vitro to characterize plaque in the human aorta. See B. Baizilai et al., "Quantitative ultrasonic characterization of nature of atherosclerotic plaques in human aorta", Circulation Research 60: 459 (1987). Using this technology in an in-vitro bath, it has been possible to distinguish fibrous, fatty, and calcific tissue.

Ultrasonic techniques have also been suggested for determining the cross-sectional area of various organs. U S Pat. Nos. 3,542,014 (Peonneau), 3,779,234 (Eggleton et al), 4,142,412 (McLeod et al), 4,237,729 (McLeod et al) 4,259,870 (McLeod et al) and 4,232,373 (Jackson et al) disclose various ultrasonic transducer arrangements for determining the cross-sectional area of internal organs. To some extent, such organs can be imaged using transducers placed on the body surface. It is possible to image the carotid arteries, the aorta and femoral arteries using these techniques. McPherson et al. have used a specialized high frequency transducer directly on the surface of the exposed human heart during cardiac surgery to provide a cross-sectional image of the coronary arteries. See D. McPherson et al. "Delineation of the Extend of Coronary Atherosclerosis by High Frequency Epicardial Echocardiography", New. E. J. of Med. 316, p. 304 (1987).

At a December, 1987 Contractors meeting of the Devices and Technology branch of the National Heart, Lung and Blood Institute, Dr. Charles Meyers reported on the performance of a feasibility study to determine if the details of the heart artery wall structure can be imaged with ultrasound. The study used a several millimeter diameter ceramic transducer on the end of a metal rod directed axially down the vessel center line. A 45° elliptical mirror was mounted a short distance from the end of the ceramic transducer on a short piece of tubing so that the sound beam was directed radially into the vessel wall. The assembly was apparently a few inches long, so that it could be inserted into sections of cadaver arteries. Mechanical rotation of the transducer assembly was used to scan the sound beam in a radial direction, (plane position indicator scan) to build up a cross-sectional image of the artery wall. A number of these images indicated that many interior details of wall structure could be seen with short pulse excitation. When lesions were examined, the fatty areas showed up as echo free and calcium showed as strongly reflecting centers. The intrusion of both kinds of regions into the normal vessel wall was quite well demonstrated. In addition, fibrous tissue growth also was delineated, since the echoes appeared to occur as streaks parallel to the direction of the fibers. Dr. Meyers reported plans to build a flexible delivery device for the subject transducer. See Meyer, et al, "Feasibility of High-Resolution, Intravascular Ultrasonic Imaging Catheters", Radiology 168:113–116 (1988). Others have also reported on ultrasound imaging of vessels using intravascular catheters. See Hodgson et al, "Validation of a New Real Time Percutaneous Intravascular Ultrasound Imaging Catheter", American Heart Association Abstract (Nov. 14–17, 1988); Graham, "Utility of an Intravascular Ultrasound Imaging Device for Arterial Wall Definition and Atherectomy Guidance", American College of Cardiology Abstract (Mar. 19–23, 1989); Kophock et al, "Intraluminal Vascular Ultrasound: Dimensional and Morphologic Accuracy", Laser and Stent Therapy in Vascular Surgery—International Congress II (Feb. 10–15, 1989); Schwarten, et al, "Endovascular US: Adjunct to Percutaneous Atherectomy", Radiology Abstract 331; "Ultrasound Imaging Catheter Hailed For Diagnostic Accuracy", Cardiology World News, page 25 (July/August 1988); EndoSonics Cathscanner I System trade literature, EndoSonics Corp. Rancho Cordova, Calif. The potential for intravascular imaging was also recently reported in Medical World News, Jan. 9, 1989 at page 33. These catheter designs are said to comprise an ultrasound probe at the end of the catheter which emits a radial signal that produces a two-dimensional image of surrounding intra- and extravascular structures. A similar report on the progress of developing intravascular ultrasound imaging catheters as small as 0.8–1 mm appears in Moretti, M., "New Diagnostic Techniques Rely on Image Processing", Laser Focus/Electrooptics, pages 198–203 (April 1988).

U.S. Pat. Nos. 3,827,115 (Bom) and 3,938,502 (Bom) disclose a heart catheter with circumferentially arranged transducers for determining intraluminal diameter. Both Bom patents disclose a catheter useful with a hollow organ such as the heart, which catheter has elements on its distal end and is capable of transmitting and receiving ultrasonic waves. It has recently been reported that intravascular ultrasonic imaging devices can produce cross-sectional images. CVR & R 20–21 (June, 1988). Although details of the catheter construction were not reported, the catheter used in creating these images is described as comprising a 20-mHz ultrasound transducer of less than one mm in diameter on its tip, which is linked with a scanner for real-time display. Apparently the subject catheter utilizes piezoelectric crystals and is too large to image coronary arteries since the involved investigator, Dr. Paul G. Yock, reportedly desires to further miniaturize the device and reduce its cost "so that the instrument can be fabricated at reasonable cost". See also Mallery et al, "Intravascular Ultrasound Imaging Catheter Assessment of Normal and Atherosclerotic Arterial Wall Thickness" JACC Volume 11, No. 2, Abstract 22A (February, 1988), wherein a 1.4 mm diameter intravascular ultrasound imaging catheter with 5 20 mHz ultrasound transducers oriented radially at its tip is reported as showing promise as a method for accurately measuring normal and diseased arterial wall thickness. See also Bom et al., "Intra-Arterial Ultrasonic Imaging for Recanalization by Spark Erosion", Ultrasound in Med. & Biol., Vol. 14, No. 4, pp. 257–61 (1988). Bom reports that a previous 3.2 mm diameter 32-elements cylindrical catheter tip transducer was too large and that diminishing its size to an outer diameter of 2 mm "would be technologically difficult and would require an integrated circuit design for multiplexing, transmitting and receiving signals." The main reason not to follow this course is described by Bom as "the expected transmission pulse transient effect masking the near-by structure echoes". Accordingly Bom discloses a 20 MHz signal element construction in combination with an acoustic mirror utilized in a transducer element of one millimeter provided with an air backing and mounted onto a metal bar. Experience gained with these preliminary trials is said to have led to the decision to design a mechanically rotating catheter tip device that would provide cross-sectional two-dimensional images. The subject catheter is described as comprising a mirror mounted on the end of a flexible wire which can be rotated. The piezoelectric element is positioned over an air backing and comprises a tip of three "mutually isolated electrodes". Three electrode wires form an open cage for the echo signals and support the catheter tip.

As seen from the above, the recently suggested designs for intravascular probes are frequently bulky, difficult and expensive to manufacture, and unlikely to be miniaturized to the degree necessary to image most of the vessels of greatest importance. Accordingly, a need exists for a miniature intravascular, ultrasonic imaging catheter which is relatively easy to fabricate, and which can be used to generate high quality cross sectional images of vascular tissue, whether or not calcified.

SUMMARY OF THE INVENTION

A novel, miniature intravascular imaging catheter is provided for use in ultrasonically imaging the walls of potentially diseased vessels of relatively small diameters. The subject catheter is composed of a flexible plastic material (PVDF) which can be spot polarized to act as a piezoelectric transducer in discrete "active" regions. Regions intermediate to the active regions remain inactive, and serve as insulators. The inherent flexibility of thin layers of PVDF permits the subject catheters to be rolled about a longitudinal axis into a multiple layer spiral embodiment, or formed into a tube in extruded embodiment. In both cases, catheters are provided which are flexible enough to serve well to image most vessels of clinical significance.

In the preferred embodiment, the electrodes needed to drive the piezoelectric material and to sense the reflected ultrasonic echoes are deposited as thin metallic films on opposing surfaces of the active regions of the PVDF layer. Conductors may be similarly deposited to connect the electrodes disposed generally at the distal end of the catheter with appropriate connections at the proximal end.

In the preferred embodiment, a plurality of discrete driving electrodes is arrayed around the distal end of the catheter. In one embodiment, a single grounding electrode is provided on the opposite surface of the PVDF layer, which grounding electrode is preferably on the outside surface where it serves as additional protection against unwanted electrical leakage. In another embodiment, each driving electrode corresponds to a discrete grounding electrode on the opposite side of the piezoelectric layer, such that the transducer can be excited in a push-pull modality. In yet a further embodiment, shielding electrodes are provided between adjacent driving electrodes, adjacent grounding electrodes, or both, to minimize coupling between the radiating elements.

In the preferred embodiments, the entire catheter is composed of an integral strip of PVDF material, thus minimizing any risk of component separation during catheter use. The catheter is further protected from its operating environment by a protective shield which acoustically couples the transducers to its surrounding fluids and/or tissue. This shield may comprise a portion of the PVDF strip itself in the spiral wound embodiment, or may consist of a separate outer sheath or coat which provides additional electrical insulation for the device. Acoustical backing materials and/or a flexible foam core forms the center of the catheter.

The resulting catheter may be used alone for diagnostic purposes, or with other diagnostic or therapeutic catheters, such as angioplasty (balloon) catheters. The catheter of the present invention is relatively easy to fabricate in relatively small diameters. This catheter design is well suited to mass production at relatively low cost, making it potentially disposable. A wide variety of transducer configurations is possible, permitting the transducer array to be customized to the particular vessel or lumen to be imaged.

Accordingly, a primary object of the present invention is the provision of novel, intravascular ultrasonic imaging catheters.

Another object of the present invention is the provision of novel methods for constructing such catheters.

These and other objects of the present invention will become apparent from the following, more detailed description of the present invention.

BRIEF DESCRIPTION OF THE FIGURES

FIG. 8 is an isometric view showing the assembly of a tubular or spiral catheter, depicting the insertion of a core prior to fusion of the PVD material into its tubular configuration;

FIG. 9 is a foreshortened view of the proximal end of a spiral wound catheter and a connector therefore;

FIG. 10 is a clamp which completes the connector assembly for use with a spiral wound catheter made in accordance with the present invention.

FIG. 11 is an isometric view of a strip useful for making a spiral wound catheter of the present invention illustrating a pattern of spot polarization and electrode placement on the plastic material.

DETAILED DESCRIPTION OF THE PREFERRED EMBODIMENTS

The present invention provides a novel ultrasound catheter for imaging the cross sections of blood vessels or other small diameter biological structures. Catheters of the present invention comprise ultrasound transducer elements arranged to radiate sound in a radial direction for examining the interior of small cylindrical structures. The general approach of using an array of transducers to image a target medium is well known in the art of ultrasonic imaging. Those of ordinary skill in the art also are familiar with a variety of techniques of collecting and displaying echo data generated from using such arrays. Such data may, for example, be displayed in real time as tissue or organ images. The primary object of the present invention is therefore to provide novel miniature ultrasonic catheters and methods of constructing same which will be useful with a variety of known or to be developed data processing and imaging schemes or approaches.

To some extent, the operating frequency of imaging transducers is known to depend upon the spatial relationship between the transducer and the body to be imaged. In the present application, the spatial resolution desired for imaging the vascular wall dictates that the catheter transducer working frequency lie between about 15-20 MHz. The round-tip amplitude attenuation at 20 MHz is estimated to be approximately 4 dB/mm.

Those of ordinary skill in the art will further appreciate that departures may be made from the materials and methods of the present invention without departing from the scope thereof, which is described more particularly in the appended claims. For example, the methods of manufacture described herein, although intended primarily as a practical means of manufacturing very small diameter catheters, could theoretically be adapted to larger structures.

The basic approach of the present invention is to integrate the conductive materials forming the transducer electrodes, any shielding electrodes and their related conductors with a plastic material which acts both as the insulating material between the conductive elements and as the piezoelectric material itself. The plastic material selected for this purpose is amenable to known spot polarization techniques. Such techniques are known to convert certain plastics, such as PVDF, into material having piezoelectric properties. Such material is capable of generating ultrasound when properly excited.

The present invention takes advantage of the above described approach to provide several different embodiments, the principal ones of which are spiral wound and tubular catheters.

Figure 1:
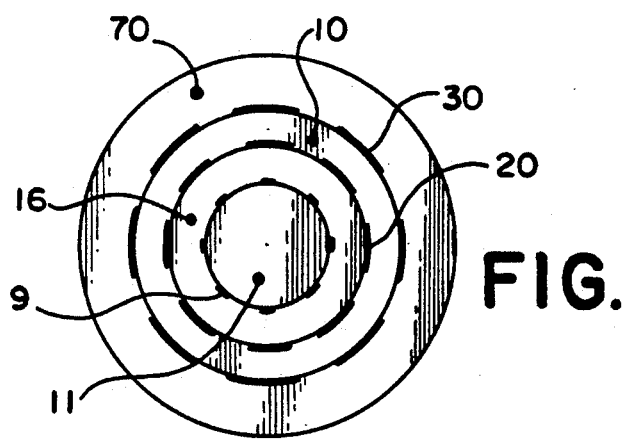
FIG. 1 is an end view of the tip of the tubular embodiment of the present invention illustrating an outer layer of unbiased and unelectroded base plastic serving as an external protective sheath under which is disposed a piezoelectric or biased electrostrictive plastic layer having discrete driving and ground electrodes disposed on opposing sides thereof, an inner layer having shielding electrodes disposed thereon, and a central core disposed in the axial center of the catheter.
Figure 2:
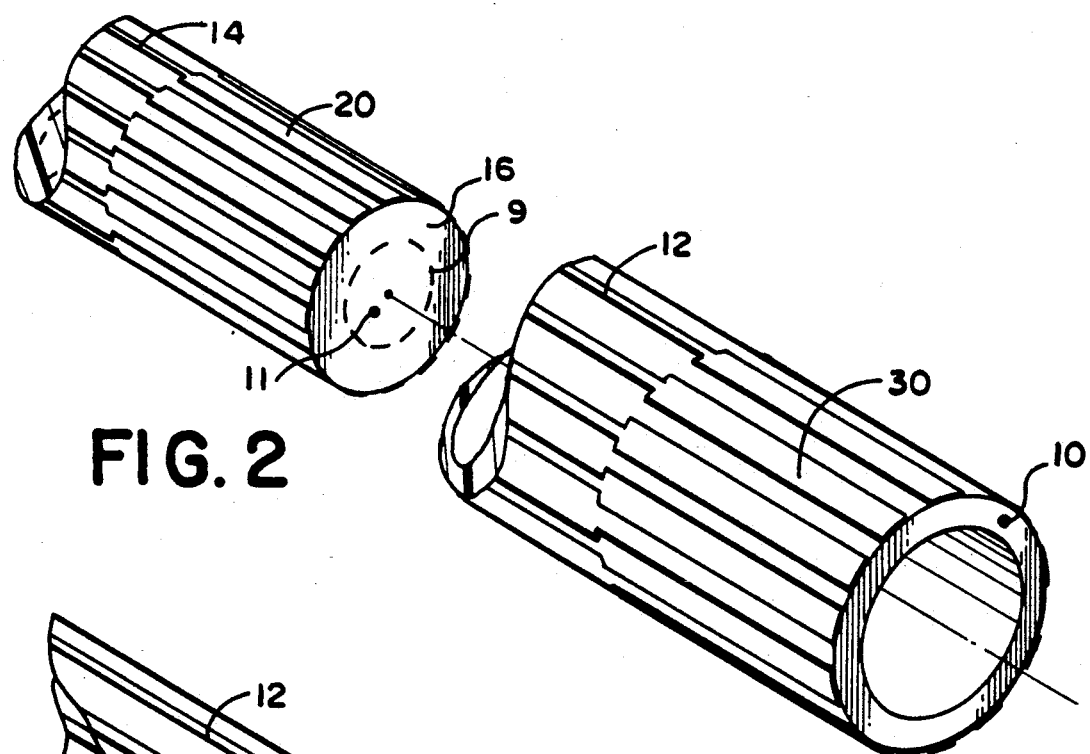
FIG. 2 is a foreshortened exploded isometric view of the core and innermost tubular layer of the catheter of FIG. 1 showing the location of the driving electrodes on the outer surface thereof, and illustrating the manner in which the two portions are assembled.
Figure 3:
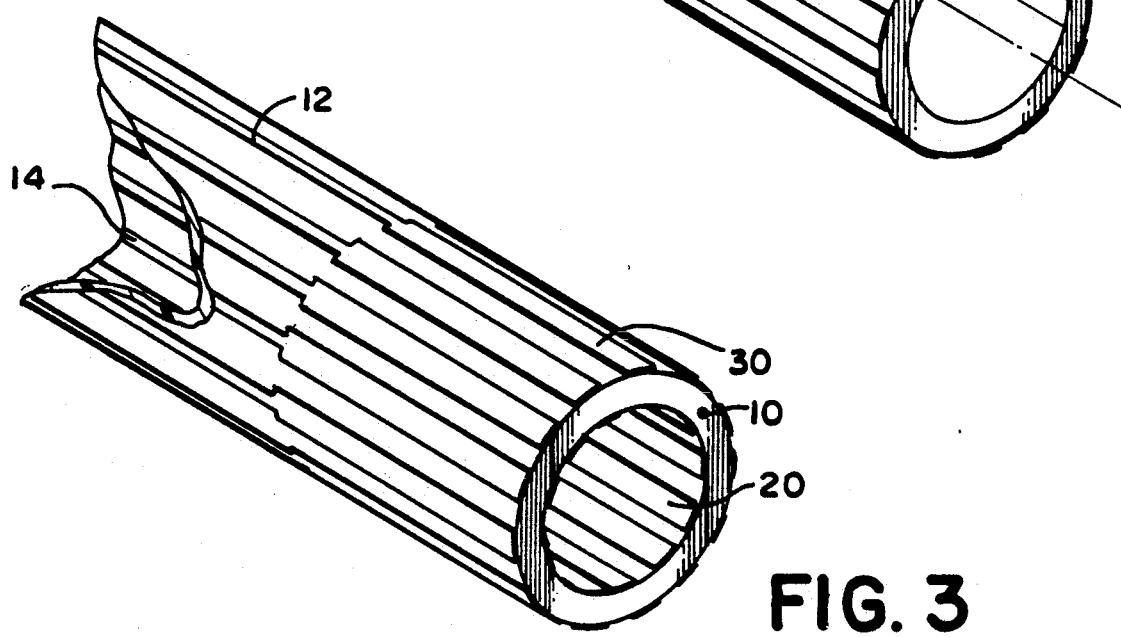
FIG. 3 is an enlarged foreshortened isometric view of the distal portion of an alternate embodiment tubular catheter in accordance with the present invention showing complementally disposed driving and grounding electrodes on opposing sides of an intermediate PVDF tube which is spot poled to provide piezoelectric transducing elements between opposing electrodes.

FIGS. 1-3 illustrate tubular embodiments of the present invention. In these embodiments, a flexible plastic tube 10 capable of being polarized to become piezoelectric in distinct regions is provided. A plurality of discrete driving electrodes 20 is disposed on a first surface of said tube to define active regions of said tube. At least one ground electrode 30 is defined on the second surface of said tube at least in the regions opposite from said driving electrodes. In the embodiments shown in FIGS. 1-3, a plurality of such electrodes is provided, one for each driving electrode 20. The tube 10 is selectively polarized to be piezoelectrically active in said active regions while remaining substantially inactive in the areas between said regions to thereby serve as an insulator. The preferred materials for constructing these catheters are polyvinyledene (PVDF) or certain PVDF copolymers which can be spot polarized to become piezoelectrically active. These copolymers include PVDF copolymer VF2/VF3. PVDF transmitters are excellent materials for use in the catheters of the present invention because they exhibit wide band performance and can produce virtually a single cycle at the excitation frequency.

One of the advantages of the present invention is that a single integral tube 10 of plastic material can be used to form substantially the entire length of a catheter which is about 120-130 cm long. As best seen in FIG. 3, electrode conductors or connectors 12 and 14 are disposed along the first and second surfaces of the catheter tube, the connectors being electrically connected respectively to the driving electrodes 20 and ground electrodes 30. Preferably, the electrodes 20,30 and these conductors or connectors 12,14 are thin metallic layers which are deposited upon the surfaces of the plastic tube 10. Accordingly, no separate connections need be made between the transducing electrodes 20,30 and their respective conductors or connectors 12,14 which extend to the proximal end of the catheter. By using this technique, the likelihood of breakage or discontinuity is minimized.

The simplest tubular embodiment, comprising just the tube 10, electrodes 20 and 30 and conductors 12 and 14, is illustrated in FIG. 3. FIG. 1 illustrates a more complex tubular embodiment wherein the basic components are supplemented with a core 11, an inner acoustically active backing material 16, and inner shielding electrodes 9. The shielding electrodes 9 may comprise discrete shielding conductors applied to the adjacent surface of the piezoelectric, or may be metallic coatings appropriately disposed on that surface. The embodiment of FIG. 1 further comprises an outer sheath or protective tube 70 which protects the electrodes 30 during use, and which acoustically couples the transducer to its surrounding media during use.

In the preferred embodiments, the central core 11 may be composed of open cell elastomeric foam. The acoustically active backing material 16 may be PVDF (unpolarized), or any other material having the desired flexibility and electrical and acoustical properties. The protective sheath 70 may be a distinct tubular layer, as shown in FIG. 1, or may be a thin coating. The protective sheath 70 may be composed of unpolarized PVDF, or other biocompatible materials having the desired degree of flexibility, acoustic transmission, and electrical insulating properties. The central core 11 may further comprise a lumen to receive a conventional guide wire. The lumen may also be used to otherwise treat or diagnose the vasculature. It is anticipated, for example, that the catheter of the present invention may be used with balloon angioplasty catheters, laser catheters, etc. to assist in locating the portion of the vessel wall to be treated, and to determine whether the applied treatment was effective.

The preferred embodiments of the present invention may be constructed sequentially from the innermost core to the outermost layer. FIG. 2 illustrates one stage in that construction, wherein the core 11 was first made with the shielding electrodes 9 disposed on the exterior surface thereof. The backing layer 16, itself a tube, is then formed around the core/shielding electrode subassembly 11,9. Next, driving electrodes 20, and their associated conductors 14, are deposited on the outside surface of the backing layer 16. The next step is illustrated in FIG. 8, wherein the subassembly shown in the left portion of FIG. 2, and designated generally as 100, is shown receiving the piezoelectric layer 10, shown in the right portion of FIG. 2 generally as 110. In this assembly step, the piezoelectric strip 110 is fed past guide 200, and through a hole formed in a jig 202. As with the other layers, this layer may be adhered to its underlying layer or tube using a suitable adhesive, such as a conductive epoxy. The method illustrated in FIG. 8 may also be used to construct spiral wound catheters, if desired.

In alternate embodiments, each tubular layer is formed as an integral tube, as for example by fusing the abutting seams thereof, or by extrusion of the molten plastic. While such a construction may minimize the degree of adhesive which may otherwise be needed for catheter assembly, in all events, it is important that the driving electrodes be aligned with the ground electrodes (when distinct ground electrodes are employed), and that the driving electrodes are properly oriented over portions of the underlying plastic layer which have been spot poled to become piezoelectric.

The thicknesses of the different layers of the preferred catheters may vary depending upon their size and the size of the vessel to be imaged. Typical dimensions for these layers would be 1-4 microns for the protective sheath; 9-50 microns (preferably about 40) microns for the poled PVDF piezoelectrically active layer, 9-30 (preferably about 20) microns for the nonpoled PVDF backing layer, with the remainder of the diameter accounted for by the foam core. The use of thinner PVDF materials is possible, although not preferred since the transmitting efficiency decreases with decreasing thickness. Thicker materials are significantly stiffer, making 50 micron thickness materials the outer desired limit for the present vascular imaging application. By contrast, the average electrode and/or connector described herein has a thickness of about 800-1000 Angstroms, making any contribution to the stiffness of the resulting catheter negligible.

The preferred electroding materials are Indium-Copper and Chromium-Gold. The adhesion of such materials to the PVDF material is critical to maximizing the performance of the design. Although chromium-nickel may be used in certain applications, this is not preferred due to prior experience which showed that those electrodes are not sufficiently flexible and may flake off relatively easily.

The protective sheath 70 should be chosen to provide the proper electrical insulation and biological compatibility. The proper electrical insulation is needed because the excitation voltage can be on the order of 100 V. In addition, coating is necessary to prevent blood clotting. It is understood that since the coating material will be immersed in blood during operation of the catheter, biological compatibility of the coating has to be acceptable. Adhesion properties of the coating are also important. In addition to liquid or solid PVDF materials, other plastic materials may prove suitable. The coating thickness may be controlled by dipping or spraying, spraying being presently preferred.

To bond the layers of the catheters disclosed, commercially available conducting epoxies are presently preferred. Such epoxies are currently available commercially as Tra-duct, or from Ciba-Geigy. Such epoxies may also be used for connecting wires to the proximal end of the conductors at the proximal catheter tip.

In designing the electrode pattern for the preferred catheters, between three and six transducing elements are presently preferred. A greater number of elements allows better wall thickness delineation to be achieved. On the other hand, the minimum spacing between the adjacent elements (approximately 50 microns) and the increased number of leads set physical limitations on the maximum number of elements.

The electrodes of the preferred embodiment may be formed on the plastic substrate using masks of the desired electrode pattern. Such masks may be ordered e.g. from Towne Laboratories, Inc., One, U.S. Highway 206, Somerville, N.J. 08876. The mask pattern may then be used in the deposition of the metallic electrodes on the PVDF film. The deposition process may be performed in vacuum deposition chamber facilities, such as those available at Drexel University, in Philadelphia, Pa.

The spot poling process is well known. JASA 69:853-859, 1981. A. S. Seleggi, S. C. Roth, D. M. Kenney, S. Edelman, C. R. Harris, "Piezoelectric Polymer Probe For Ultrasonic Applications," *IEEE Tran. Sound Ultrasonic*, SU-29, PP. 370-377, 1982. See, G. E. Harris. The poling procedure requires the manufacturing of custom shaped electrodes. There are certain advantages to using the masking procedure, including the ease and precision of manufacture. This precision will eliminate variability between different catheters, a major drawback with prior designs.

Alternatively, the electroding pattern can be obtained using the mask and a chemical etching process. This alternative process can replace the necessity for spot poling of the PVDF film, because it removes unwanted electrode areas from fully electroded film. The etching process has the disadvantage of leaving previously poled areas of PVDF intact, even in areas where the electroding material has been removed. This is presently not preferred, since the acoustic and electric coupling between the adjacent elements should be minimized. In the spot poling procedure, virtually no electric field is generated between the adjacent elements. In etching, although the preexisting electrodes are removed, the piezoelectric properties of the material itself are left intact.

In instances where a single element transducer is desired, the element should have a sensitive element area of about 1.0 mm$^2$. The element should be mounted on the curvature corresponding to a radius of approximately 0.5 mm.

The extrusion process described above offers the promise for successful design of subminiature catheters which can be made in diameters of less than 1 mm. In these catheters, the material may be either PVDF or VF2/VF3 co-polymer, the latter offering a higher coupling coefficient, and thus better piezoelectric properties. The spot poling technique can be used, and subsequently the desired electrode pattern can be sputter deposited. Inside the tubing, a thin copper or platinum wire can be used to conduct the signal. In this embodiment, the entire tip of the catheter can be piezoelectrically active. An alternate embodiment of this design is shown in FIG. 11, wherein the entire distal end of the catheter is poled to be active, and wherein "stripes" 12 and 30 of metal are deposited along the length of the catheter to connect the electrodes to its proximal end.

Figure 4:
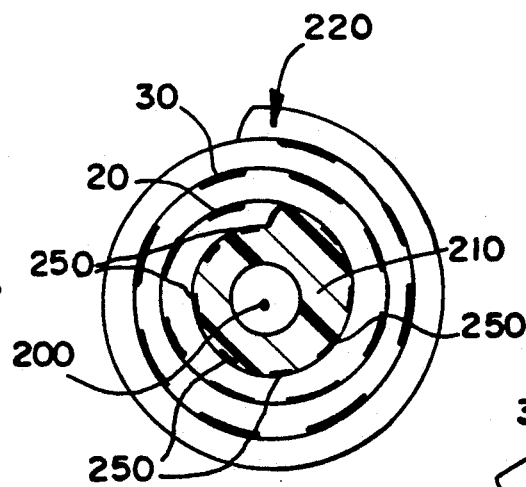
FIG. 4 is an end view of the spiral embodiment of the present invention.
Figure 5:
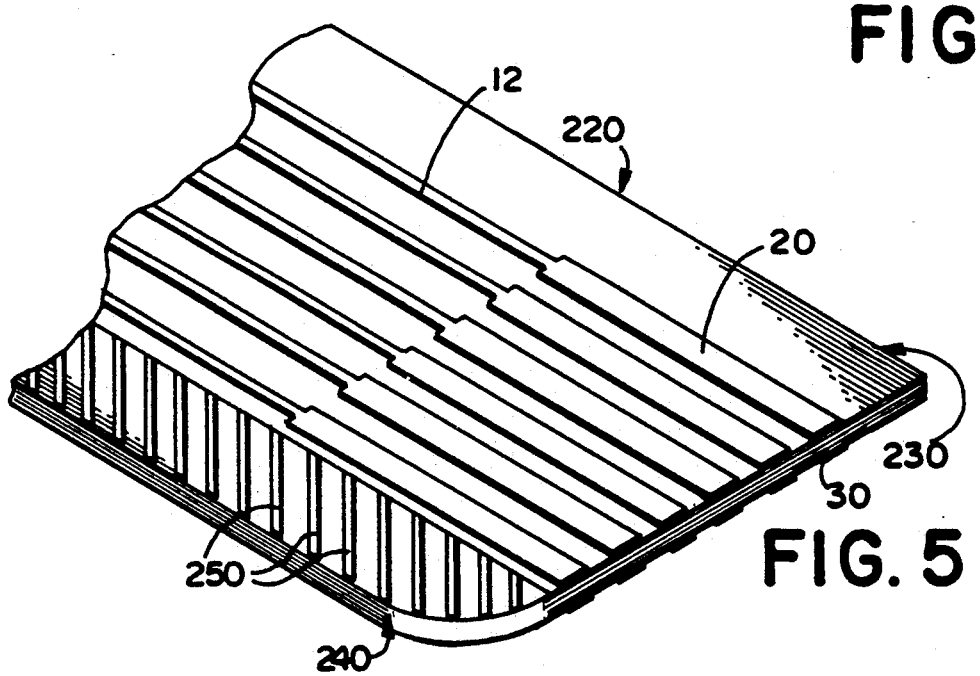
FIG. 5 is an isometric foreshortened view of the PVDF strip which is wound to form the catheter of FIG. 4.
Figure 7:
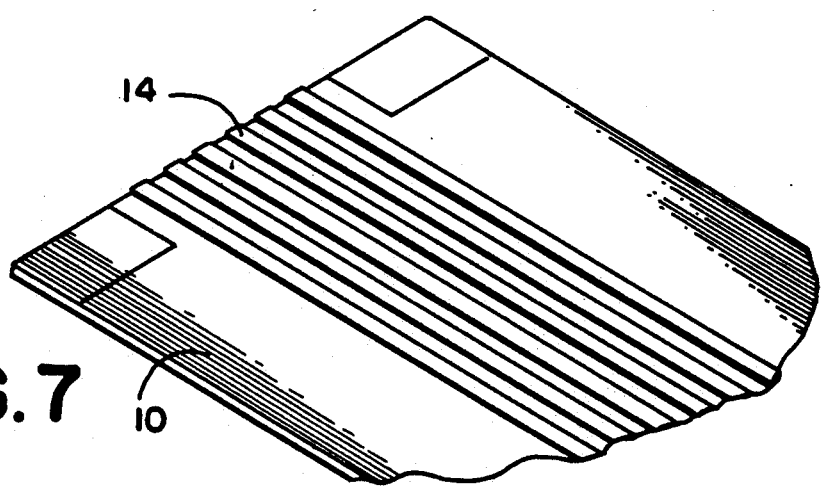
FIG. 7 is a foreshortened view of the proximal end of the PVDF strip of FIG. 5.

FIGS. 4, 5, 7 and 11 relate to spiral rolled embodiments of the present invention. These embodiments are based upon the concept of forming the entire catheter, or a number of its operative components, from and on the surfaces of a strip of plastic material which is then rolled about its longitudinal axis to form a "spiral rolled" catheter. In FIG. 4, a catheter is illustrated wherein a central lumen 200 is surrounded by a foam core 210. Around the core 210 is wrapped a single strip of plastic material, such as the strip, designated generally 220, illustrated in FIG. 5. As seen in FIG. 5, the strip 220 has unpolled portions 230 and 240 extending longitudinally down each of its sides. The distal end of portion 240, when rolled, becomes the acoustic backing element. As shown in FIGS. 4 and 5, the backing element 240 preferably has shielding electrode(s) 250 deposited thereon. Driving electrodes 30 are again formed on one side of the piezoelectrically active strip, and grounding electrodes 20 on the other side. Each electrode portion is connected to the proximal end of the catheter by conductors or connectors 12 and 14 (not illustrated in FIG. 5), which are preferably extended regions formed by the same metal deposition process which formed the electrodes.

When the strip 220 is rolled, as may be performed continuously as shown in FIG. 8, a catheter having a distal tip end view as shown in FIG. 4 will be produced. In the catheter of FIG. 4, the first circumference of the spiral orients the shielding electrodes into position, the second disposes the ground and driving electrode portions in an intermediate layer, and the third provides the protective sheath.

Figure 6:
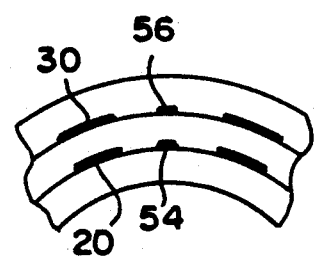
FIG. 6 is a greatly enlarged partial end view of the distal portion of a catheter in accordance with the present invention showing an alternate location for the guard or shielding electrodes disposed between adjacent driving and grounding electrodes.

FIG. 6 discloses an alternate embodiment arrangement of shielding electrodes which may be used in place of, or in addition to, a central shielding electrode configuration. In this embodiment, the shield electrodes 54 and 56 are located intermediate of pairs of the driving electrodes 20 and ground electrodes 30. These shielding electrodes 54,56 are connected to the proximal end of the catheter by connectors or conductors which extend down the length of the catheter similar to the conductors 12 illustrated in FIG. 5

Accordingly, a novel method of making an intravascular catheter is provided comprising the steps of providing a strip of flexible plastic material capable of being polarized in discrete regions to act as a piezoelectric transducer in those regions, said strip having proximal and distal ends, adhering electrodes to opposing surfaces of said strip near its distal end to define active regions thereon; spot poling said active regions of said strip to provide at least one piezoelectric transducing element of said strip; attaching connectors to said electrodes for electrically connecting said electrodes to connections at the proximal end of said catheter; spiral winding said strip around its longitudinal axis to form a spiral having a diameter of less than about 1 mm; and fixing said spiral in its wound position to provide a catheter capable of use in ultrasonic imaging.

FIGS. 9 and 10 disclose a proximal end connector for connecting catheters of the present invention to associated electronics and display equipment. In FIG. 9, the inner portion of the connector is shown having a small body 300 which ma be slidably inserted into a complementally configured receiving portion of the proximal catheter end, which body 300 has defined on its outer surface a plurality of conductive portions 310 which will contact and connect appropriate ones of the connectors on the interior side of the appropriate catheter layer to the wires 320 shown protruding from the back of the connector. In order to complete the connection, a sleeve 350, is provided, which will clamp over the outer surface of the proximal end of the catheter to connect abutting metallic portions of the connector and catheter, to again connect corresponding catheter connections with metallic connectors and wires on the connector body. Note that both the interior and exterior connections are mating connections.

As seen from the above, a variety of improved catheter designs is provided, each of which is useful in the imaging of the cross section of a relatively small artery or vein of a patient during a transcutaneous procedure. The subject catheters are relatively simple and easy to produce. Their low cost may facilitate true disposability. The imaging quality which is generated using these catheters, however, is expected to be superior.

As used herein, PVDF refers to polyvinylidene (di)-fluoride plastic. Such plastics are commercially available in sheets as thin as 9 microns from the Pennwalt Company, Philadelphia, Pa. Alternative source: Solvay, Brussels, Belgium. The term "piezoelectric" as used herein refers to the ability of a material to generate an electric signal when exposed to a mechanical force (such as an acoustic wave), and conversely to exert a force (e.g. generate an acoustic wave) when excited by an external voltage source.

We claim:

1. An intravascular ultrasonic imaging catheter for imaging the cross section of a vessel, comprising:
    (a) a flexible plastic tube polarized in distinct regions to become piezoelectric in those regions;
    (b) a plurality of discrete driving electrodes disposed on a first surface of said tube to define active regions of said tube; and,
    (c) at least one ground electrode defined on the second surface of said tube at least in the regions opposite from said driving electrodes;
said tube being selectively polarized to be piezoelectrically active in said active regions while remaining substantially inactive in the areas between said regions.

2. The catheter of claim 1 wherein said tube comprises PVDF.

3. The catheter of claim 1 wherein said tube comprises a PVDF copolymer.

4. The catheter of claim 1 wherein said tube extends to form substantially the entire length of said catheter, and wherein said catheter further comprises electrode connectors disposed along the first and second surfaces of said tube, said connectors being electrically connected respectively to said driving and ground electrodes.

5. The catheter of claim 1 further comprising a sheath means for providing a protective barrier around said tube.

6. The catheter of claim further comprising an acoustical backing portion disposed within said tube at least adjacent to said active regions.

7. The catheter of claim 1 wherein said at least one ground electrode comprises a plurality of discrete grounding electrodes, at least one for each driving electrode.

8. The catheter of claim 7 further comprising a plurality of shielding electrodes defined on the first and second surfaces of said active material between adjacent ones of said active and ground electrodes.

9. The catheter of claim 8 further comprising a plurality of shield electrode connectors for electrically connecting said shield electrodes to ground.

10. The catheter of claim 1 wherein said grounding electrode is a single grounding electrode disposed along the entire second surface of said plastic in the region opposite to said driving electrodes, and wherein the said second surface is the outer surface of said catheter.

11. The catheter of claim 1 further comprising a central core.

12. The catheter of claim 11 said core comprises elastomeric foam.

13. The catheter of claim 11 wherein said core further comprises means for further diagnosing or treating said vessel.

14. The catheter of claim 1 wherein said core further defines a lumen.

15. The catheter of claim 1 wherein said electrodes are metallic coatings deposited on said plastic surfaces.

* * * * *